United States Patent [19]

Puskas et al.

[11] 4,415,479
[45] Nov. 15, 1983

[54] PALLADIUM ON CARBON CATALYST FOR PURIFICATION OF CRUDE TEREPHTHALIC ACID

[75] Inventors: Imre Puskas, Glen Ellyn; David E. James, Batavia, both of Ill.

[73] Assignee: Standard Oil Company (Indiana), Chicago, Ill.

[21] Appl. No.: 316,336

[22] Filed: Oct. 29, 1981

[51] Int. Cl.$^3$ .................... B01J 23/44; C07C 51/42
[52] U.S. Cl. ........................... 502/85; 562/487
[58] Field of Search ............... 252/447, 444, 472, 460, 252/466 PT, 431 N

[56] References Cited

U.S. PATENT DOCUMENTS

| | | | |
|---|---|---|---|
| 3,318,891 | 5/1967 | Hausman et al. | 252/431 C |
| 3,629,145 | 12/1971 | Morikawa et al. | 252/460 |
| 4,052,336 | 10/1977 | Montfoort et al. | 252/444 |
| 4,093,559 | 6/1978 | Fernholz et al. | 252/447 |
| 4,239,653 | 12/1980 | Bodnar et al. | 252/447 |
| 4,260,829 | 4/1981 | Horner et al. | 568/434 |

Primary Examiner—P. E. Konopka
Attorney, Agent, or Firm—William C. Clarke; William T. McClain; William H. Magidson

[57] ABSTRACT

A catalyst and process for purifying crude terephthalic acid wherein the catalyst comprises palladium metal crystallites deposited upon a carbon support wherein the catalyst is prepared by contacting a carbonaceous support with an aqueous solution of a palladium amine complex in the presence of acetic acid.

18 Claims, No Drawings

PALLADIUM ON CARBON CATALYST FOR PURIFICATION OF CRUDE TEREPHTHALIC ACID

BACKGROUND OF THE INVENTION

Purification of crude terephthalic acid by hydrogenation over a suitable catalyst is well-known. Hydrogenation offers the easiest route for removal of 4-carboxybenzaldehyde (4-CBA) impurity from the crude terephthalic acid (TA). This invention is directed to an improved process for the hydrogenation of crude terephthalic acid in the presence of a catalyst prepared by utilizing palladium metal deposited upon an active carbon support from a complex salt which reacts with the carbon to produce a catalyst of improved activity and/or selectivity in hydrogenating 4-carboxybenzaldehyde.

Catalysts comprising a Group VIII metal of the Periodic Table of Elements upon an inert carrier are known for use in various hydrogenation reactions. They are usually prepared by impregnating a support material with a solution of a compound of a Group VIII metal and reducing the impregnated compound to the metal. Catalyst improvements typically have been directed to obtaining increased hydrogenation activity rather than increased activity and/or selectivity in hydrogenating specific compounds.

It is an object of the instant invention to provide an improved method for preparing a catalyst compound of a Group VIII metal. A particular object is to provide a method for preparing such catalysts having increased catalytic activity and/or selectivity in the reduction of 4-carboxybenzaldehyde. Another object is to provide a catalytic composition which comprises crystallites of catalytically active palladium upon the surface of a porous support material wherein a catalyst of improved activity and/or selectivity is obtained for use in a process for reduction of 4-carboxybenzaldehyde in purification of crude terephthalic acid containing up to 10,000 ppm of 4-carboxybenzaldehyde. Still further objects will be apparent from the following specification.

The field of this invention accordingly relates to Group VIII metal catalysts for hydrogenation and purification of terephthalic acid suitable for polyester polymers and copolymers useful in the manufacture of textile fibers. These polymers and copolymers have been made by condensing terephthalic acid with ethylene glycol and other dihydric alcohols.

As with other supported catalysts, the activity and selectivity of a Group VIII metal catalyst upon a carrier depends on numerous factors such as the amount of Group VIII metal or metals present in the catalyst, the type of support, the method by which the Group VIII metal or metals are deposited and the distribution of the metal or metals on the support.

Such Group VIII catalysts are limited in their ability to selectively hydrogenate impurities in crude terephthalic acid, especially 4-carboxybenzaldehyde. Users of terephthalic acid, such as textile fiber manufacturers, often put a rigorous limitation on the allowable concentration of 4-carboxybenzaldehyde in terephthalic acid.

Typically, Group VIII metal catalysts, such as palladium catalysts, are prepared by causing a palladium salt to be adsorbed from a solution onto a carrier. In one procedure as is taught in U.S. Pat. No. 2,857,337, the salt is thereupon treated with a water-soluble metal hydroxide or basic carbonate which is thereafter reduced to metallic palladium by reducing agents such as formaldehyde, glucose, hydrazine, glycerine and the like. Other conventional methods of preparing palladium catalysts have been taught. U.S. Pat. No. 2,802,794 teaches impregnation of an activated alumina support material with a solution of a compound of the platinum metal group and reducing the impregnated compound to the metal. The preconditioned activated alumina is obtained by heating a hydrated alumina to a temperature of up to 800° C. whereby a microporous alumina is obtained.

U.S. Pat. No. 3,138,560 to Keith, et al., teaches that when sodium tetrachloropalladate or palladium chloride is added to many carbon supports, most of the palladium is immediately deposited as a shiny film of metallic palladium. Catalysts so prepared generally have low activities and it has been theorized that the palladium compound is directly reduced to palladium metal by the presence of functional groups, such as aldehydes or free electrons on the carbon surface. Palladium catalysts are accordingly advantageously prepared by fixing the palladium as an insoluble compound prior to reduction to avoid the problems of migration and crystallite growth which can occur when a metal is reduced from solution. Keith '560 teaches inclusion of an oxidizing agent, such as hydrogen peroxide to hydrolyze the palladium prior to reduction by the carbon, thus obtaining improved palladium dispersion and a highly active catalyst. U.S. Pat. No. 3,288,725 to Aftandilian teaches that catalysts produced by deposition of a transition metal compound upon an inert particulate solid and subsequent reduction often have a disadvantage in that uniform deposition of the transition metal compound upon the surface of the inert particulate is accomplished with great difficulty. Hence, when the metal compound is reduced, the metal atoms deposited on the surface thereof are not exposed, are therefore not completely reduced and maximum potential catalytic activity is not achieved. Aftandilian '725 teaches that reaction of the metal compound with a particulate surface having a suitable hydroxyl group content, followed by reduction with a borohydride produces an improved catalyst. U.S. Pat. No. 3,737,395 to Arnold, et al., teaches a process for preparing a catalyst which avoids formation of gels which cause lower activity. The catalysts are taught as having uniform and controlled deposition of palladium or platinum and a metallic promoter onto particulate carbon. An aqueous slurry is formed of the palladium or platinum compound and the water soluble metallic promoter. A precipitant is then added to precipitate the palladium or platinum and the metallic promoter, followed by co-reduction of both with a mild reducing agent such as formaldehyde, hydrazine, sodium formate, glucose or hydrogen. U.S. Pat. No. 3,271,327 to McEvoy, et al., teaches a process for depositing palladium upon the surface of a nonporous support material wherein the palladium forms a thin, firm and adherent coating, thus obtaining maximum catalytic activity by means of a thin, peripheral distribution of palladium oxide in the support material. U.S. Pat. No. 3,318,891 to Hausmann, et al., teaches preparation of palladium diacetate which in turn reacts with pyridine, aniline and benzylamine to give well-defined crystalline products useful as catalysts for liquid phase oxidation reactions. U.S. Pat. No. 3,328,465 to Spiegler, teaches the preparation of palladium metal deposited on nonporous carbon support admixed with a porous carbon. The resulting catalyst is taught as resulting in a rate of hydrogenation about twice that of a hydrogenation process using the same amount of palladium deposited on a nonporous carbon. Previously, carbon used for support of palladium had been mainly porous carbon of vegetable or animal origin. Due to the high porosity of the carbon, some of the palladium became trapped in the pores and did not contribute to the activity of the catalyst. Another disadvantage was that such porous catalysts became fouled with the products of hydrogenation.

The impurities in crude terephthalic acid prepared from p-xylene are partially oxidized products such as toluic acid and 4-carboxybenzaldehyde. These impurities are usually present in significant amounts. Toluic acid is not a particularly harmful impurity, in that it is readily removed by cooling and crystallizing terephthalic acid solutions containing it. Impurities other than toluic acid, but particularly 4-carboxybenzaldehyde, are difficult to remove from terephthalic acid as such, but are more readily separated from terephthalic acid as derivatives. Purification of crude terephthalic acid containing a high concentration of 4-carboxybenzaldehyde (4-CBA) is usually accomplished by converting 4-CBA by hydrogenation over a suitable catalyst to products which can be easily separated from the terephthalic acid by crystallization. However, only with great difficulty can the level of 4-CBA be reduced to levels below the limitation required by textile manufacturers. 4-Carboxybenzaldehyde is a particularly undesirable impurity because it acts as a chain-stopper during polyesterification of terephthalic acid.

Accordingly, a catalyst and process are highly desirable whereby impurities in crude terephthalic acid such as 4-carboxybenzaldehyde are hydrogenated to very low levels by selective reduction to readily separable compounds.

A number of techniques and processes have been developed to purify terephthalic acid by hydrogenation using palladium or platinum catalysts conventionally prepared as described above. Various devices are utilized to obtain the desired selectivity and activity in hydrogenating 4-carboxybenzaldehyde.

U.S. Pat. No. 3,522,298 to Bryant, et al., teaches a process wherein crude terephthalic acid is admixed with an inert gaseous carrier such as steam. The vapor mixture is contacted at a temperature of from 600° to 1000° F. with hydrogen in the presence of a catalyst such as a Group VIII metal upon a carbonaceous support, i.e., palladium upon powdered carbon. Vaporized terephthalic acid is separated by condensation from other constituents in the vapor, e.g., steam, other impurities. U.S. Pat. No. 3,542,863 to Zimmerschied teaches that hot formic acid treatment of palladium metal on charcoal catalyst controls the activity and/or reactivity in instances where initial activity of a fresh catalyst is excessive and causes over-hydrogenation of aromatic rings or carboxylic acid groups or where catalysts have become deactivated due to use with oxygenated hydrocarbons. U.S. Pat. No. 3,584,039 to Meyer teaches purification of terephthalic acid by hydrogenation in aqueous liquid phase upon a Group VIII metal on carbon in the presence of hydrogen followed by crystallization from the mother liquor. U.S. Pat. No. 3,591,629 to Stancell, et al., teaches that a phenylbenzene treated catalyst of a Group VIII metal on activated carbon particles minimizes the conversion of terephthalic acid in the presence of hydrogen while effecting high conversions of 4-carboxybenzaldehyde contaminating the commercial acid. U.S. Pat. No. 3,607,921 to Stancell teaches that contact of crude terephthalic acid with carbon monoxide in the presence of palladium on carbon support effects a high percentage conversion of 4-carboxybenzaldehyde contaminating the acid. Surface area of the metal upon the carbon support is taught as being extremely high, to 120 square meters per gram. U.S. Pat. No. 3,726,915 to Pohlmann teaches that copper based on palladium in palladium/carbon catalysts increases the activity of palladium/carbon catalysts in the hydrogenation of 4-carboxybenzaldehyde acid. U.S. Pat. No. 3,799,976 to Nienburg, et al., teaches purification of terephthalic acid containing 4-carboxybenzaldehyde by heating an aqueous mixture of the crude acid with formic acid in contact with a Group VIII metal as catalyst. U.S. Pat. No. 4,260,817 to Thompson, et al., teaches a method for purifying crude terephthalic acid by hydrogenating the crude acid to make toluic acid from 4-carboxybenzaldehyde and p-xylene from terephthalyl dialdehyde wherein the reduction takes place in two stages, the aldehyde radical forming an alcohol radical and in turn forming a methyl radical. The catalyst comprises two Group VIII metals on carbon particles.

Accordingly, it is well-known that crude terephthalic acid containing 4-carboxybenzaldehyde and other impurities can be purified by hydrogenation over a Group VIII metal on carbon catalyst. However, more selective catalysts and processes are highly desirable wherein crude terephthalic acid containing high levels of 4-carboxybenzaldehyde is selectively hydrogenated to contain very low levels of 4-carboxybenzaldehyde.

SUMMARY

A catalyst and process for producing a purified terephthalic acid wherein 4-carboxybenzaldehyde content is reduced to very low levels, to less than 100 parts per million, in a standard laboratory evaluation, which comprises reacting in liquid phase a mixture of hydrogen and crude terephthalic acid at a temperature of from about 100° C. to about 300° C. and a pressure from about 200 to 1500 psi in the presence of a catalyst compound comprising palladium metal crystallites deposited upon a carbon support wherein the catalyst is prepared by contacting a porous carbonaceous support with an aqueous solution of a palladium amine complex in the presence of acetic acid, palladium content is not greater than 0.6 (wt) percent of total catalyst weight, and palladium metal crystallites are predominantly less than 35 angstroms (Å) in longitudinal measurement.

DETAILED DESCRIPTION OF THE INVENTION

The process of the instant invention relates to purification of terephthalic acid wherein 4-carboxybenzaldehyde (4-CBA) content is reduced to very low levels, to less than 100 parts per million (ppm) in a standard laboratory test. The general method requires use of a palladium catalyst prepared by reducing a precursor comprising a complex palladium salt upon a porous carbonaceous support. The complex salt is prepared by dissolving a salt of palladium in aqueous amine solution and adding acetic acid to the resulting solution.

It has been found that catalysts prepared by the above method are effective in purifying crude terephthalic acid. Moreover, the palladium on carbon catalyst is selective in reducing 4-carboxybenzaldehyde content to low levels.

Palladium is the preferred metal for the catalyst of this invention, but other metals of Group VIII of the Periodic Table of Elements and possessing activity for hydrogenation are suitable in general, such as ruthenium, osmium, iridium, rhodium and platinum. The pertinent Periodic Table of Elements can be found on the inside of the back cover of HANDBOOK OF CHEMISTRY AND PHYSICS, 46th Edition, Robert C. Weast, Editor, Chemical Rubber Company, Cleveland, Ohio (1965).

Ammonia and organic amines can be used to make a water soluble complex salt of palladium suitable for preparation of catalysts of the instant invention. The organic amines can be aliphatic, aromatic, or heterocyclic. Preferred organic amines are methylamine, pyridine, picolines, lutidines, etc. Use of these amines causes palladium to be adsorbed quickly and almost quantitatively on coconut charcoal in contrast to use of ammonium complexes of palladium salts, or ethylene diamine complexes of palladium salts, wherein adsorption of palladium on coconut charcoal under similar conditions is only in the 37 to 68% range. However, catalysts so prepared are still active catalysts in the hydrogenation of 4-carboxybenzaldehyde.

As indicated, the novel process of the present invention is carried out using an organic carboxylic acid, either monocarboxylic or polycarboxylic. This includes both lower aliphatic saturated fatty acids which are liquids at room temperature (about 25° C.) and, particularly, saturated fatty monocarboxylic acids having from 2 to 5 carbon atoms, inclusive, such as acetic acid, propionic acid, butyric acid, isobutyric acid, n-valeric acid and mixtures thereof, and higher aliphatic saturated fatty acids which, although solids at room temperature, can be dissolved in the presence of amines, such as lauric acid, myristic acid, palmitic acid, stearic acid, malonic acid, glutaric acid, pimelic acid, azelaic acid and mixtures thereof. Unsaturated acids such as acrylic acid, dibasic acids such as oxalic acid and inorganic acids such as nitric acid may be suitable for this purpose.

For reasons unknown, a more selective catalyst is obtained by the addition of an organic carboxylic acid such as acetic acid to an aqueous solution of an amine complex of a palladium salt during catalyst preparation.

The porous carbonaceous support or substrate is any suitable granular carbon having a surface area of at least 600 m$^2$/g (N$_2$, BET method). Activated carbon granules of high surface area prepare from plant, animal or mineral sources can be used. While carbon granules are preferred, the method of this invention would also extend to carbon used in the form of pellets and other particulate forms. Preferably the substrate is activated carbon of plant or animal origin, most preferably of coconut charcoal.

The palladium catalyst of this invention is characterized by being prepared from aqeuous solutions of palladium-amine complexes in the presence of an organic carboxylic acid, preferably a lower aliphatic saturated fatty acid, more preferably acetic acid, wherein the acid and amine are present in substantially equimolar quantities. The palladium is adsorbed upon the surface of the porous carbonaceous support over a period of from 1 to 24 hours. The resulting composition is washed, filtered and dried. The catalyst can be used immediately for terephthalic acid purification. However, in a laboratory evaluation, a water slurry of the freshly-prepared catalyst is heated under hydrogen, for a period of about 1¾ to 2 hours at a temperature of 270° C. After the composition is cooled, the catalyst particles are filtered from the water slurry and dried under vacuum at approximately 80° C.

The catalysts of the process of the instant invention are believed to comprise palladium crystallites predominantly less than 35 Å in longitudinal measurement upon a support of carbonaceous material of plant origin, animal origin or mineral origin.

For reasons which are not understood, it has been found that preparation of a catalyst comprising palladium deposited upon a porous carbonaceous support from an aqueous solution of a palladium-amine complex in the presence of an organic carboxylic acid results in palladium crystallites predominantly of less than 35 angstrom units (Å) in longitudinal measurement as measured by X-ray diffraction apparatus. Only crystallites with longitudinal measurement larger than 35 Å can be detected due to the limit of resolution by the X-ray diffraction apparatus.

For reasons which are not understood, it has been found that hydrogenation of crude terephthalic acid with a catalyst comprising palladium metal upon a porous carbonaceous support prepared from an aqueous solution of a palladium chloride-amine complex wherein the adsorption of palladium on a porous carbonaceous support such as activated carbon particles occurs in the presence of an organic carboxylic acid purifies crude terephthalic acid by reducing impurities of 4-carboxybenzaldehyde (4-CBA) much better than with a catalyst prepared similarly but in the absence of an organic carboxylic acid.

It has been found that the use of an amine and an organic carboxylic acid in approximately equimolar quantities in preparation of the instant catalyst results in a hydrogenation catalyst which reduces 4-CBA content of crude terephthalic acid to a level below 100 ppm in a standard laboratory test. The ratio of amine to acetic acid is important. As the ratio becomes less than 1:1, i.e., the molar quantity of acetic acid relative to the molar quantity of amine, the catalyst performance declines and the levels of 4-CBA after hydrogenation of crude terephthalic acid increase to levels which are unacceptable in terephthalic acid for fiber use.

Surface area of supported metallic palladium can be calculated from X-ray diffraction data.

Alternatively, the surface area of the palladium metal deposited on porous carbonaceous material can be calculated from carbon monoxide adsorption measurements. Palladium surface area of fresh catalysts of the present invention can be as high as 340 m$^2$/g palladium, or even higher, as determined by either method.

A method has also been discovered of preparing supported metallic palladium whose crystallites are predominantly less than 35 Å in size. This method consists of depositing palladium upon solid supporting granules of porous carbonaceous material material from a solution of a palladium-amine complex salt in the presence of organic carboxylic acid.

Palladium uptake by carbon granules using the method of preparing the instant catalyst is limited by the amount of palladium salt used to less than 1.0 (wt) percent of total catalyst weight, preferably less than 0.60 (wt) percent of total catalyst weight. Higher concentrations are of little avail because in the process of reducing 4-CBA to toluic acid, the higher concentration of palladium metal do little to improve the efficiency of the catalyst.

The palladium salt utilized in the present invention is normally a palladium halide, such as palladium chloride, palladium bromide and palladium iodide, or palladium acetate dissolved in water with the aid of an amine. An organic carboxylic acid is then added to the solution.

For example, in preparation of the instant invented catalyst, granular activated vegetable charcoal is washed to remove charcoal fines. The washed vegetable charcoal is covered with water, and the water layer is agitated and slowly (dropwise) the palladium salt solution containing the amine and acetic acid is added. The resulting mixture is kept under agitation at a temperature of from 0° C. to 100° C. for a period of from 0.5 to 24 hours. The resulting catalyst particles are filtered from the mixture, washed with water at a temperature of from 0° to 100° C. and dried under vacuum of 100 mm Hg and 80° C. for a period of 12 hours or less.

This catalyst is ready for use in a commercial process. However, to standardize the catalyst evaluation and to avoid measurement of a possible misleading initial catalyst activity, the catalyst is treated with hydrogen at a temperature of 270° C. The catalyst particles are added to water in an autoclave and hydrogen gas under pressure is introduced into the autoclave. The mixture of catalyst particles, hydrogen gas and water is heated to a temperature of 270° C. for a period of about 1¾ to 2 hours. The mixture is then cooled.

The activity and selectivity of each catalyst were evaluated thereupon under standard laboratory conditions which simulated purification of terephthalic acid from the 4-carboxybenzaldehyde impurity under full-scale plant process conditions. 4-Carboxybenzaldehyde content of a terephthalic acid plant process stream can vary widely. Standard laboratory test conditions accordingly were used to measure activity and selectivity of catalyst compositions of the instant invention.

In summary, the instant invention comprises a method of preparing a catalyst composition, the catalyst composition prepared thereby and a catalytic hydrogenation process for hydrogenating crude terephthalic acid containing up to 10,000 ppm of 4-carboxybenzaldehyde in the presence of the catalyst composition, water and hydrogen at a temperature of from about 100° C. to about 300° C. and a pressure of from about 200 to 1500 psig and recovering purified terephathalic acid from the mixture. The catalyst is prepared by contacting porous carbonaceous support granules with an aqueous solution of an amine and a palladium salt in the presence of an organic carboxylic acid wherein the mole ratio of the acid to the amine is at least 0.75 and preferably in substantially equimolar quantities. Concentration of the amine is sufficient to solubilize the palladium salt. The palladium salt is selected from the group consisting of palladium chloride, palladium iodide, palladium bromide and palladium acetate. The organic carboxylic acid can be saturated, unsaturated or dibasic, preferably selected from the group having 2 to 5 carbon atoms such as acetic acid, n-valeric acid, acrylic acid and oxalic acid. The porous carbonaceous support or substrate is any suitable granular carbon having a surface area of at least 600 m$^2$/g (N$_2$, BET method). The amine can be ammonia or an organic amine. Aliphatic, aromatic or heterocyclic organic amines are suitable such as methylamine, pyridine, picolines, lutidines, etc.

The invention will be further illustrated by reference to the following specific examples.

EXAMPLE I

A number of catalysts were prepared to illustrate the present invention. In all cases approximately 4 to 8 mesh granular carbons of coconut shell origin were washed with distilled water to remove fines and then drained. The carbons were contacted with the solutions as indicated below, washed, drained and dried at a temperature of approximately 80° C.

Catalyst A. Granular coconut charcoal (12 grams) was washed with distilled water to remove the carbon fines. The water was decanted and the moist charcoal was transferred into a 3-necked 300 ml flask. Distilled water (40 ml) was placed over it. A glass stirrer was installed which had a small paddle immersed into the water layer above the carbon. The stirrer was turned on. Palladium chloride (0.202 g) was dissolved in a mixture of distilled water (22.0 ml) and conc. ammonium hydroxide solution (3.0 ml with 28-30 (wt)% NH$_3$). This solution was added dropwise from a dropping funnel to the stirred charcoal-water mixture. The stirring was continued for 2¾ hours. Then the catalyst was filtered, washed with hot water and dried in vacuum at 80° C.

Catalyst B. Granular coconut charcoal (18.0 g) was washed with distilled water to remove the carbon fines. The water was decanted and the moist charcoal was transferred into a 3-necked 300 ml flask. Distilled water (60.0 ml) and acetic acid (0.05 ml) were placed over it and stirred with a paddle located in the water layer above the carbon. PdCl$_2$ (0.153 g) was added to water (40.0 ml) containing pyridine (0.5 ml). Acetic acid (0.20 ml) was added. Acetic acid/pyridine mole ratio was 0.66. From a dropping funnel, the PdCl$_2$/pyridine/acetic acid solution was introduced dropwise and stirred for 1¾ hours. Then the resulting catalyst was filtered, washed with distilled water and dried in vacuum at 80° C.

Catalyst C. In the method of Catalyst B, Catalyst C was prepared from PdCl$_2$, ammonia and acetic acid as follows: PdCl$_2$ (0.202 g), water (60 ml), ammonia (3.0 ml with 28-30 (wt) % NH$_3$), acetic acid (3.6 ml). Acetic acid/ammonia mole ratio was 1.13.

Catalyst D. In the method of Catalyst B, Catalyst D was prepared from PdCl$_2$, pyridine, and acetic acid as follows: PdCl$_2$ (0.153 g), water (100 ml), pyridine (0.75 ml), acetic acid (0.55 ml). Acetic acid/pyridine mole ratio was 1.00.

Catalyst E. In the method of Catalyst D, Catalyst E was prepared from PdCl$_2$ and pyridine as follows: PdCl$_2$ (0.153 g), water (100 ml), pyridine (0.75 ml).

Before evaluation, the above catalysts were subjected to "simulated aging" because evaluations of fresh catalysts can give misleading results.

Distilled water (150 ml), the catalyst (6.0 g) and hydrogen gas at 200 psig were charged into a 300 ml rocking autoclave, heated to 270° C. and held at the temperature for 1¾ hours. After cooling, the catalyst was recovered and dried in vacuum oven at 80° C.

The above catalysts were evaluated for terephthalic acid (TA) purification as follows: Catalyst and crude terephthalic acid were charged into a 300 ml rocking autoclave as follows: 12.9 g of crude TA, containing 7900 ppm 4-carboxybenzaldehyde (4-CBA); 150 ml distilled water; 0.17 g of catalyst under evaluation and 200 psig hydrogen gas. The reactor was heated to 250°

C. and held at that temperature for 3½ hours. After cooling, the TA crystals were filtered, washed with 100 ml distilled water and dried in vacuo at 105° C. The purified TA was analyzed by liquid chromatography and by polargraphy. Results are in Table I. A commercially available palladium/carbon catalyst was used as a comparative example.

TABLE I

| Catalyst and Run No. | Reagents of the Pd Solution | 4-CBA (ppm) | Acetic Acid/ Amine Ratio | (wt) % Pd | Pd Content >35 Å % (a) |
|---|---|---|---|---|---|
| Commercial | Unknown | 153 | — | 0.50 | 68 |
| A 5054-180-1 | PdCl$_2$/NH$_3$ | 428 | 0 | 0.25 | 20 |
| B 5293-5-1 | PdCl$_2$/Pyridine/Acetic Acid | 394 | 0.66 | (b) | — |
| C 5054-183-1 | PdCl$_2$NH$_3$/ Acetic Acid | 91 | 1.13 | 0.36 | 7 |
| D 5293-33-1 5054-125-1 | PdCl$_2$Pyridine/Acetic Acid | 34 47 | 1.00 1.00 | (b) 0.50 | — 0 |
| E 5054-186-1 | PdCl$_2$/Pyridine | 245 | 0 | 0.53 | 0 |

(a) Measurements after hydrogen treatment at 270° C.
(b) Estimated 0.5 (wt)%.

What is claimed is:

1. A method of making a catalyst comprising crystallites of catalytically active palladium adsorbed on the surface of a porous carbonaceous support material comprising activated carbon granules having a surface area of at least 600 m$^2$/g wherein said palladium crystallites are predominantly less than 35 angstroms (Å) in longitudinal measurement, and palladium content is less than 1.0 (wt)% of total catalyst weight, which method comprises adsorbing catalytically active palladium crystallites on the surface of activated carbon granules by contacting said granules with an aqueous solution of an amine and a palladium salt in the presence of an organic carboxylic acid wherein concentration of said amine is sufficient to solubilize said palladium salt and mole ratio of said acid to said amine is at least 0.75 wherein said palladium reacts with said carbon to produce said catalyst.

2. The method of claim 1 wherein said palladium salt is selected from the group consisting of palladium chloride, palladium bromide, palladium iodide and palladium acetate.

3. The method of claim 1 wherein said palladium salt is palladium chloride.

4. The method of claim 1 wherein said acid has from 2 to 5 carbon atoms.

5. The method of claim 1 wherein said acid is selected from the group consisting of acetic acid, propionic acid, butyric acid, isobutyric acid, n-valeric acid and mixtures thereof.

6. The method of claim 1 wherein said acid is acetic acid.

7. The method of claim 1 wherein said amine is selected from the group consisting of ammonia, methylamine, pyridine, the picolines and the lutidines.

8. The method of claim 1 wherein said amine is pyridine.

9. The method of claim 1 wherein mole ratio of said acid to said amine is approximately 1.0.

10. A catalyst composition for purification of terephthalic acid which comprises crystallites of catalytically active palladium adsorbed upon a porous carbonaceous support material comprising activated carbon granules having a surface area of at leat 600 m$^2$/g wherein said palladium crystallites are predominantly less than 35 angstroms (Å) in longitudinal measurement and palladium content is less than 1.0 (wt)% of total catalyst weight, wherein said catalyst is prepared by adsorbing catalytically active palladium crystallites upon the surface of activated carbon granules by contacting said granules with an aqueous solution of an amine and a palladium salt in the presence of an organic carboxylic acid wherein concentration of said amine is sufficient to solubilize said palladium salt, and the mole ratio of said acid to amine is at least 0.75 wherein said palladium reacts with said carbon to produce said catalyst composition.

11. The composition of claim 10 wherein said palladium salt is selected from the group consisting of palladium chloride, palladium bromide, palladium iodide and palladium acetate.

12. The composition of claim 10 wherein said palladium salt is palladium chloride.

13. The composition of claim 10 wherein said acid has from 2 to 5 carbon atoms.

14. The composition of claim 10 wherein said acid is selected from the group consisting of acetic acid, propionic acid, butyric acid, isobutyric acid, n-valeric acid and mixtures thereof.

15. The composition of claim 10 wherein said acid is acetic acid.

16. The composition of claim 10 wherein said amine is selected from the group consisting of ammonia, methylamine, pyridine, the picolines and the lutidines.

17. The composition of claim 10 wherein said amine is pyridine.

18. The composition of claim 10 wherein mole ratio of said acid to said amine is approximately 1.0.

* * * * *